United States Patent
Bergmann et al.

(10) Patent No.: US 8,183,004 B2
(45) Date of Patent: May 22, 2012

(54) DETERMINATION OF SHORT-CHAIN SRL ALCOHOL DEHYDROGENASE (DHRS4) AS A BIOMARKER FOR INFLAMMATIONS AND INFECTIONS

(75) Inventors: Andreas Bergmann, Berlin (DE); Joachim Struck, Berlin (DE); Monika Uhlein, Berlin (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 787 days.

(21) Appl. No.: 11/908,346

(22) PCT Filed: Mar. 6, 2006

(86) PCT No.: PCT/EP2006/002043
§ 371 (c)(1),
(2), (4) Date: Sep. 11, 2007

(87) PCT Pub. No.: WO2006/094747
PCT Pub. Date: Sep. 14, 2006

(65) Prior Publication Data
US 2009/0136973 A1    May 28, 2009

(30) Foreign Application Priority Data

Mar. 11, 2005   (DE) .................. 10 2005 011 421

(51) Int. Cl.
  *G01N 33/68*   (2006.01)
(52) U.S. Cl. ............................. 435/7.4; 435/26
(58) Field of Classification Search .................. None
  See application file for complete search history.

(56) References Cited

FOREIGN PATENT DOCUMENTS
WO   WO 2004003162  A2 *  1/2004

OTHER PUBLICATIONS
Song et al., Int. J. Cancer, 120:1618-1626, 2007.*

* cited by examiner

*Primary Examiner* — Nita M Minnifield
*Assistant Examiner* — Brian J Gangle
(74) *Attorney, Agent, or Firm* — Heslin Rothenberg Farley & Mesiti P.C.

(57) ABSTRACT

The present invention relates to the use of short-chain SRL alcohol dehydrogenase (DHRS4, SEQ ID NO: 1) and peptides thereof as humoral biomarkers for the diagnostic detection and prognosis of the course, and also monitoring the course and therapy of septic inflammations and infections.

4 Claims, 8 Drawing Sheets

Figures 1A, 1B:
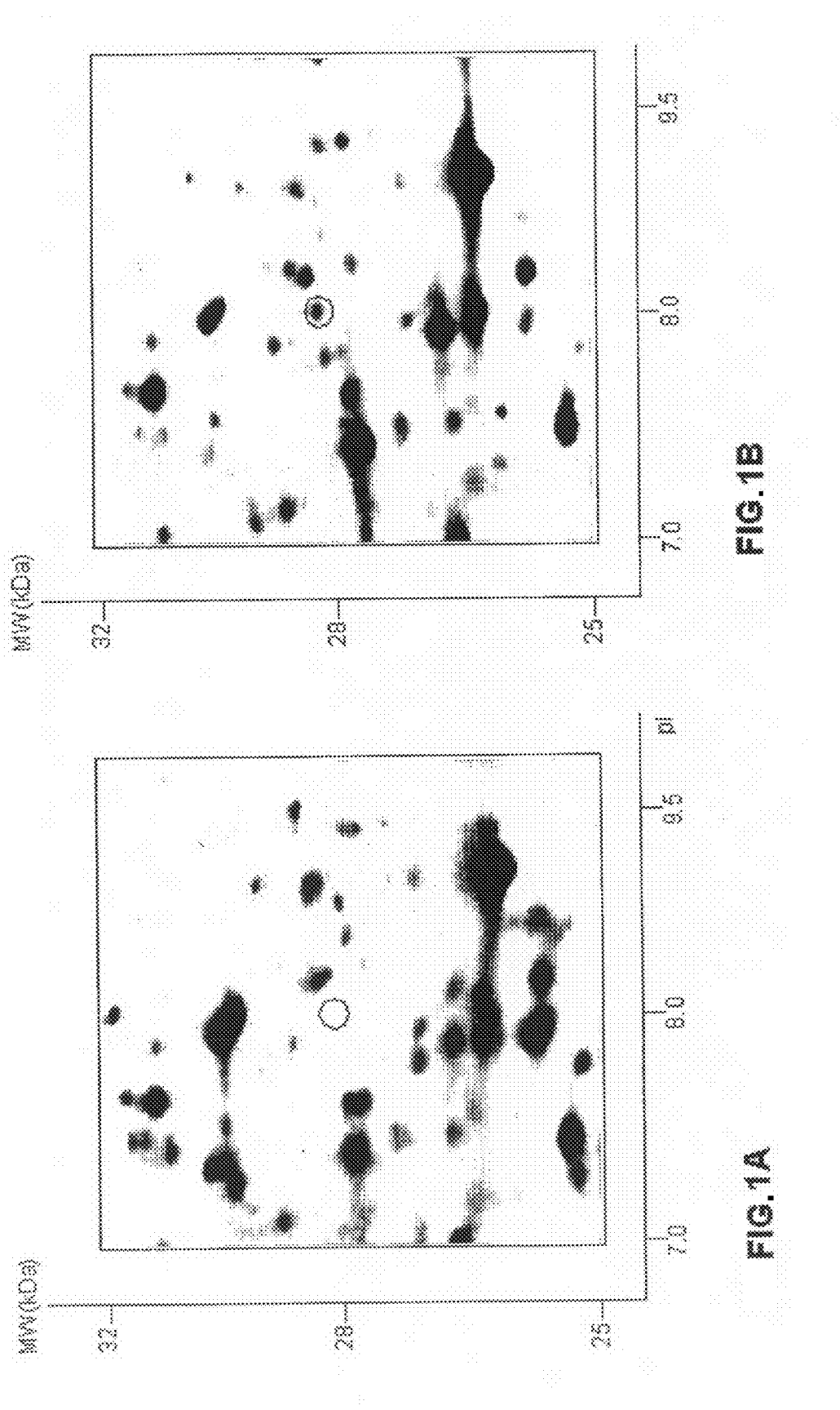

```
         10          20          30          40          50          60
          |           |           |           |           |           |
MHKAGLLGLC ARAWNSVRMA SSGMTRRDPL ANK VALAT AS TD GIGFAIAR RLA QDGA HVV
                                    ß1(A)      α1(B)           ß2(B)

70          80          90         100         110         120
          |           |           |           |           |           |
VSS RKQ QNVD QAVATL QGEG LSVTGTV CHV GKA EDRER LV ATAVKLH GGI D ILVSN AAVN
    α2(C)                       ß3(C)     α3(D)                ß4(D)

130         140         150         160         170         180
          |           |           |           |           |           |
PFFGSIMDVT EEVWDKTLDD NVKAPALMTK AVVPEMEK RG G GSVVIV SS I AAFSPSPGFS
                      α4(E)                     ß5(E)

190         200         210         220         230         240
          |           |           |           |           |           |
PYNVSKTALL GLTKTLAIEL APRN IRVNCL APG LIKT SFS RMLWMDKEKE ESMKETLRIR
     α5(F)                 ß6(F)

250         260         270
          |           |           |
RLGE PEDCAG IVSFLC SEDA SYIT GETVVV GGGTPSRL
      α6(G)              ß7(G)
```

FIG. 3

```
sp|Q9BTZ2|DHS4_HUMAN   MASSGMTRRDPLANKVALVTASTDGIGFAIARRLAQDGAHVVVSSRKQQNVDQAVATLQG
sp|Q13268|DHS2_HUMAN   -SSTGIDRKGVLANRVAVVTGSTSGIGFAIARRLARDGAHVVISSRKQQNVDRAMAKLQG
                        :**:*: ,. *::,**,*:*******:*::*****:*:*.*** sp|Q9BTZ2|DHS4_HUMAN   EGLSVTGTVCHVGKAEDRERLVATAVKLHGGIDILVSNAAVNPFFGSIMDVTEEVWDKTL
sp|Q13268|DHS2_HUMAN   EGLSVAGIVCHVGKAEDREQLVAKALEHCGGVDFLVCSAGVNPLVGSTLGTSEQIWDKIL
                        *****:*,**********:*:*:::.**:*:.:.:**:.*..:*:;:** * sp|Q9BTZ2|DHS4_HUMAN   DINVKAPALMTKAVVPEMEKRGGGSVVIVSSIAAFSPSPGFSPYNVSKTALLGLTKTLAI
sp|Q13268|DHS2_HUMAN   SVNVKSPALLLSQLLPYMENRRG-AVILVSSIAAYNPVVALGVYNVSKTALLGLTRTLAL
                        .:***:***;  . ::* **:* * *:::*******:.*  ..:. **********:***:

sp|Q9BTZ2|DHS4_HUMAN   ELAPRNIRVNCLAPGLIKTSFSRMLWMDKEKEESMKETLRIRRLGEPEDCAGIVSFLCSE
sp|Q13268|DHS2_HUMAN   ELAPKDIRVNCVVPGIIKTDFSKVFHGNESLWKNFKEHHQLQRIGESEDCAGIVSFLCSP
                        ****::*****:.**:***:**:.:.  ::.  :::*:**..**********.

sp|Q9BTZ2|DHS4_HUMAN   DASYITGETVVVGGGTPSRL   (SEQ ID NO.: 11)
sp|Q13268|DHS2_HUMAN   DASYVNGENIAVAG-YSTRL   (SEQ ID NO.: 8)
                        ****:.**.:*.*   .:**
```

FIGURE 7A

```
sp|Q9BTZ2|DHS4_HUMAN    MASSGMTRRDPLANKVALVTASTDGIGFAIARRLAQDGAHVVVSSRKQQN
sp_vs|Q9BTZ2-2|Q9BTZ2   MASSGMTRRDPLANKVALVTASTDGIGFAIARRLAQDGAHVVVSSRKQQN
sp_vs|Q9BTZ2-3|Q9BTZ2   MASSGMTRRDPLANKVALVTASTDGIGFAIARRLAQDGAHVVVSSRKQQN
                         ************************************************** sp|Q9BTZ2|DHS4_HUMAN    VDQAVATLQGEGLSVTGTVCHVGKAEDRERLVATAVKLHGGIDILVSNAA
sp_vs|Q9BTZ2-2|Q9BTZ2   VDQAVATLQGEGLSVTGTVCHVGKAEDRERLVATAVKLHGGIDILVSNAA
sp_vs|Q9BTZ2-3|Q9BTZ2   VDQAVATLQGEGLSVTGTVCHVGKAEDRERLVAT---------------
                         ********************************* sp|Q9BTZ2|DHS4_HUMAN    VNPFFGSIMDVTEEVWDKTLDINVKAPALMTKAVVPEMEKRGGGSVVIVS
sp_vs|Q9BTZ2-2|Q9BTZ2   VNPFFGSIMDVTEEVWDK-------------------------------
sp_vs|Q9BTZ2-3|Q9BTZ2   -------------------------------------------------- sp|Q9BTZ2|DHS4_HUMAN    SIAAFSPSPGFSPYNVSKTALLGLTKTLAIELAPRNIRVNCLAPGLIKTS
sp_vs|Q9BTZ2-2|Q9BTZ2   --------------------------------------------------
sp_vs|Q9BTZ2-3|Q9BTZ2   -------------------------------------------------- sp|Q9BTZ2|DHS4_HUMAN    FSRMLWMDKEKEESMKETLRIRRLGEPEDCAGIVSFLCSEDASYITGETV
sp_vs|Q9BTZ2-2|Q9BTZ2   ----LWMDKEKEESMKETLRIRRLGEPEDCAGIVSFLCSEDASYITGETV
sp_vs|Q9BTZ2-3|Q9BTZ2   ----LWMDKEKEESMKETLRIRRLGEPEDCAGIVSFLCSEDASYITGETV
                            ****************************************** sp|Q9BTZ2|DHS4_HUMAN    VVGGGTPSRL   (SEQ ID NO.: 11)
sp_vs|Q9BTZ2-2|Q9BTZ2   VVGGGTPSRL   (SEQ ID NO.: 9)
sp_vs|Q9BTZ2-3|Q9BTZ2   VVGGGTPSRL   (SEQ ID NO.: 10)
                         **********
```

FIGURE 7B

DETERMINATION OF SHORT-CHAIN SRL ALCOHOL DEHYDROGENASE (DHRS4) AS A BIOMARKER FOR INFLAMMATIONS AND INFECTIONS

CROSS REFERENCE TO RELATED APPLICATIONS

This application is a 371 filing of PCT International application no. PCT/EP2006/002043 filed Mar. 6, 2006 and published in German as WO 2006/094747 on Sep. 14, 2006 which claims the priority of German application no. 10 2005 011 421.0 filed Mar. 11, 2005. The disclosures of these applications and all other patents, published applications and other references cited herein are hereby incorporated by reference in their entirety.

The present invention relates to methods for diagnostic detection and for prognosis and monitoring of the course and therapy of inflammations and infections, in which a biomarker which is novel for the stated indications is determined. In particular, the invention relates to methods of said type in which the diagnosed inflammations and infections are part of the complex course of a septic pathological process (systemic inflammations of infectious aetiology; sepsis).

In the following description, terms such as "diagnosis" or "diagnostic" are used in principle as simplifying overall terms which, unless otherwise evident from the context, are also intended to include more specific differential diagnosis and applications for prognosis/early prognosis and monitoring of the course and therapy of the diseases discussed.

The present invention has its starting point in intensive research work by the Applicant in relation to further improvements of the diagnosis and therapy of sepsis.

There is a scientific relationship in material terms and by definition between sepsis and inflammations. Very generally, certain physiological protective reactions of the organism against various external effects, such as, for example, injuries, burns, allergens, infections by microorganisms, such as bacteria and fungi and viruses, against foreign tissues which trigger rejection reactions, or against certain inflammation-triggering endogenous states of the body, for example in autoimmune diseases and cancer, are designated as inflammations.

When inflammations are part of a misdirected reaction of the body to certain endogenous processes, such as, for example, in autoimmune diseases, and/or are of a chronic nature, or when they have reached systemic proportions, as in the case of systemic inflammatory response syndrome (SIRS), or in the case of a severe sepsis caused by infection, the inflammations may become the actual pathological process which may even become an acute threat to life when the physiological processes typical of inflammation reactions grow out of control, as in SIRS and sepsis.

In systemic inflammations, as in the case of a sepsis or of septic shock, the inflammation-specific reaction cascades spread in an uncontrolled manner over the whole body and become life-threatening in the sense of an excessive immune response. Regarding the present knowledge about the occurrence and the possible role of individual groups of endogenous inflammation-specific substances, reference is made, for example, to A. Beishuizen et al., "Endogenous Mediators in Sepsis and Septic shock", Advances in Clinical Chemistry, vol. 33, 1999, 55-131; and C. Gabay et al., "Acute Phase Proteins and Other Systemic Responses to Inflammation", The New Journal of Medicine, vol. 340, no. 6, 1999, 448-454. Since the understanding of sepsis, and hence also the recognized definitions, have changed and been refined in recent years, reference is also made to K. Reinhart et al., "Sepsis and septischer Schock [Sepsis and septic shock]", in: Intensivmedizin, Georg Thieme Verlag, Stuttgart, New York, 2001, 756-760, where a modern definition of the term sepsis is given, and in particular to Mitchell M. Levy et al., "2001 SCCM/ESICM/ACCP/ATS/SIS International Sepsis Definition Conference", in: Crit. Care Med 2003, vol. 31, no. 4, 1250-1256. Regarding the importance of the clinical picture of "severe sepsis", reference is furthermore made to Niels C. Riedemann et al., The Enigma of Sepsis, J. Clin. Invest. 112: 460-467 (2003). A more recent summary of the criteria and definitions for a sepsis and closely related clinical pictures is also to be found at url talessin.de/scripte/medizin/sepsis1.html. In the present Application, the term sepsis is used in a comprehensive sense, which includes in particular sepsis, severe sepsis and septic shock, based on the definitions as they appear in said publications for septic clinical pictures of severely ill patients in intensive care units.

While at least in the European region systemic bacterial infection detectable by a positive blood culture long characterized the term sepsis, sepsis is now understood primarily as being systemic inflammation which is caused by infection but which, as a pathological process, has great similarities with systemic inflammations which have other causes.

Said change in the understanding of sepsis is based on changes in the diagnostic approaches. Thus, the direct detection of bacterial pathogens has been replaced or supplemented by complex monitoring of laboratory parameters and haemodynamic parameters with the use of computer-aided so-called score systems (e.g. APACHE II SCORE: APACHE stands for "Acute Physiology and Chronic Health Evaluation"; cf. G. Pilz et al., Krankenpflege-Journal 29 (1981), pages 483-492, or the introduction of the patent DE 42 27 454 C1) and more recently in particular via the detection of certain endogenous substances involved in the sepsis process or the inflammatory process, i.e. specific "biomarkers".

Among the large number of mediators and acute phase proteins, in particular those whose occurrence is very specific for sepsis or certain phases of a sepsis and whose concentrations change drastically and diagnostically significantly and which moreover have the stabilities required for routine determinations, in particular ex vivo, and reach high concentrations values are suitable for diagnostic purposes. The reliable correlation of pathological process (sepsis) with the respective biomarker is of primary importance for diagnostic purposes, without it being necessary for its role in the complex cascade of endogenous substances involved in the sepsis process always to be known specifically. There is, however, increasing interest in the determination of novel particular biomarkers which (also) permit an assignment of sepsis patients to groups with related causes of the disease or a similar expected course of the disease, in the manner of a "stratification", so that, from the spectrum of possible therapeutic measures, the most suitable ones can be applied. In this context, reference may additionally be made to John C. Marshall et al., Crit Care Med 2003, vol. 31, no. 5, 1560-1567.

An established endogenous substance particularly suitable as a sepsis biomarker is procalcitonin (PCT). Procalcitonin is a prohormone whose serum concentrations reach very high values under the conditions of a systemic inflammation of infectious aetiology (sepsis), while it is virtually undetectable in healthy persons. High values of procalcitonin are moreover reached at a relatively early stage of a sepsis, so that the determination of procalcitonin is also suitable for early diagnosis of a sepsis and for early differentiation of a sepsis caused by infection from severe inflammations which have other causes. The determination of procalcitonin as a sepsis marker is a subject of the publication by M. Assicot et al., "High serum procalcitonin concentrations in patients with sepsis and infection", The Lancet, vol. 341, no. 8844, 1993, 515-518; and the patents DE 42 27 454 C2 and EP 0 656 121 B1 and U.S. Pat. No. 5,639,617. Reference is expressly made to said patents and to early literature references mentioned in said publication, for supplementing the present description.

A current discussion of the use of biomarkers, including the biomarker PCT, in sepsis diagnosis is also to be found in the review by Shawn D. Carrigan et al., "Toward Resolving the Challenges of Sepsis Diagnosis" in Clinical Chemistry 50:8, August 2004, 1301-14.

The availability of the sepsis marker procalcitonin has given considerable impetus to sepsis research, and intensive efforts are currently being made to find further biomarkers which can supplement the procalcitonin determination and/or can provide additional information for the purposes of precise diagnosis or differential diagnosis or stratification.

However, the search for potential novel sepsis biomarkers is complicated by the fact that often very little or nothing is known about the exact function or about the exact reasons for the occurrence of certain endogenous substances which are involved in the sepsis process.

Initial results of the experimental testing of a fruitful purely hypothetical approach to the determination of further potential sepsis markers are to be found in DE 198 47 690 A1 or WO 00/22439 of the Applicant. There, it is shown that, in sepsis, not only the concentration of the prohormone calcitonin is increased but significantly increased concentrations can also be observed for other substances which can be counted among the peptide prohormones or which are fragments of such prohormones and have an immunoreactivity typical of such prohormones.

The present Application is the result of another fruitful, purely experimental approach in the search for further sepsis-specific biomolecules. This is based on the fact that a pathological state which can be designated as artificial sepsis is induced in primates (baboons) by administration of an endotoxin or by infection with bacteria, and endogenous substances of a peptic or protein nature which are found only in the "septic" baboons and which therefore represent potential sepsis-specific biomarkers are then determined by comparison of the gel electrophoresis protein spot samples of endotoxin-treated and of untreated baboons. The primate model was chosen owing to the very great similarity of the physiology of primates and humans and the high cross-reactivity with many therapeutic and diagnostic human reagents.

As described more exactly in the experimental section of prior patent applications of the Applicant, a number of protein spots identifiable only in the treated animals is found after experimental induction of an artificial sepsis in baboons by endotoxin administration (LPS from Salmonella Typhimurium) and working-up of tissue of the treated animals by 2D gel electrophoresis. The protein products corresponding to the spots are isolated from the electrophoresis gel and investigated by mass spectrometry (especially by means of tandem mass spectrometry).

Inter alia, the proteins "inflammin" (WO 02/085937) CHP (WO 03/005035), soluble cytokeratin-1 fragments (sCY1F; WO 03/002600), the protein LASP-1 (WO 03/089934) and enzymes such as aldose-1-epimerase (mutarotase: WO 03/048780), glycine N-acyl transferase (GNAT; WO 03/04871) and soluble carbamoyl phosphate synthetase 1 (CPS 1; WO 03/08993) were identified as novel sepsis markers by said method, as described for the first time in prior German and European patent applications of the Applicant, in addition to sepsis markers already discussed in the literature.

A discussion of the related method of proteome analysis and the results which were obtained for a sepsis marker established using the method, which can be determined in the form of a mid regional fragment of the precursor of the hormone ANP (atrial-natriuretic peptide), is published in J. Struck et al., Immuno-analyse & biologie spécialisée 19 (2004) 131-137.

The content of said prior Applications of the Applicant and of said relevant publication is to be regarded as a supplementary part of the disclosure of the present Application by the express reference to these Applications and Publications.

The basis of the present invention is that, in an investigation of the type described using liver extracts of baboons, a substance which occurs only in the extracts of the baboons treated with LPS but is absent in healthy baboons was isolated, which substance could be identified—as explained in more detail in the experimental section—as short-chain SRL alcohol dehydrogenase (SCAD-SRL or DHRS4).

Accordingly, the present invention relates, in the widest sense, to the use of short-chain SRL alcohol dehydrogenase (DHRS4) as a humoral biomarker for diagnostic detection and for the prognosis and monitoring of the course and the therapy of inflammations and infections, in particular of those which are part of the complex course of a septic pathological process.

As will be described in more detail in the experimental section, a peptide substance which could be identified as short-chain SRL alcohol dehydrogenase (DHRS4) was identified in investigations by the Applicant.

DHRS 4 ("dehydrogenase/reductase (SDR family) member 4", synonyms: SCAD-SRL ("short-chain alcohol dehydrogenase" with the C-terminal sequence SRL), peroxisomal short-chain alcohol dehydrogenase, etc.) belongs to a large family of NAD- or NADP-dependent oxidoreductases (short-chain dehydrogenases/reductases family (SDR)) (1) (see url sanger.ac.uk/cgi-bin/Pfam/getacc?PF00106.) These enzymes comprise about 250 to 300 amino acids and are generally present as homodimers or homotetramers. Typically, the SDRs contain two domains: one which binds the coenzyme (NAD or NADP) and the other which binds the substrate and which determines the substrate specificity and is involved in the catalysis. The substrate specificity of the DHRS4 of interest here has not been experimentally demonstrated. On the basis of the sequence similarity, however, it is presumed that DHRS4 reduces all-trans-retinal and 9-cis-retinal. Further substrates could be alkyl phenyl ketones and alpha-dicarbonyl compounds having aromatic rings (such as pyrimidine-4-aldehyde, 3-benzoylpyridine, 4-benzoylpyridine, menadione and 4-hexanoylpyridine) (see url us.expasy.org/cgi-bin/niceprot.pl?q9nv08).

DHRS4 is coded by a gene on chromosome 14 (see url genecards.bcgsc.bc.ca/cgi-bin/carddisp?DHRS4&search=dhrs4&suff=txt). The amino acid sequence of DHRS4 has been derived from the associated cDNA sequence. The literature contains various interpretations regarding the n-terminal region of the protein. Thus, for example, Clark et al. give the sequence comprising 278 amino acids according to SEQ ID No: 1 (2). Other authors regard the beginning of the protein only at methionine in position 18 of the sequence according to SEQ ID No: 1 (3).

If the longer variant is taken as a basis, a signal sequence which could indicate the secretion of the protein can be identified at the n-terminus (2). Results of Fransen et al. tend to suggest a peroxisomal localization which is indicated by the C-terminal tripeptide SRL. Such a C-terminal structure is known as PTS (peroxisomal targeting sequence) (4).

DHRS4 is evidently expressed in various tissues/organs (see url genecards.bcgsc.bc.ca/cgi-bin/carddisp?DHRS4&search=dhrs4&suff=txt).

Furthermore, various alternative splicing variants have been described for DHRS4: currently, 30 differently spliced transcripts and accordingly 30 different translation products are predicted by NCBI. (see url ncbi.nlm.nih.gov/IEB/Research/Acembly/av.cgi?db=human&c=locusid&l=10901). However, only two additional variants are described in the database SWISSPROT.

WO 0153486 predicts possible glycosylation and myristoylation sites in DHRS4, which however have not been experimentally demonstrated.

In the present Application the designation DHRS4 is intended to include not only monomeric or multimeric proteins according to SEQ ID No: 1 but also splicing variants and fragments and other post translationally modified variants, in particular those which show an immunoreactivity corresponding to DHRS4 in the assays described below.

In pathophysiological contexts, WO 0153486 discloses that, inter alia, DHRS4 is overexpressed in certain cancer cells and could therefore serve as a point of attack for the therapy of cancer and diagnosis from tissue samples. A relationship with infections and septic pathological processes is, however, not indicated.

This is done for the first time in the present Application which relates in particular to the use of the new discoveries for in vitro (ex vivo) diagnosis.

The determination of DHRS4 for diagnostic purposes in the biological fluids is preferably effected ex vivo with the aid of immunodiagnostic assay methods (ligand binding assays; immunoassays).

Of course, assuming the required specificity and sensitivity, any ligand binding assays/immunoassays operating according to known principles can be used for the quantitative or semi-quantitative determination of DHRS4 in biological fluids, in particular from the circulation, such as serum or plasma.

In a preferred embodiment the method is carried out as a heterogeneous sandwich immunoassay in which a first DHRS4-binding antibody is immobilized on an arbitrary solid phase, for example the walls of coated test tubes (e.g. of polystyrene; "coated tubes"; CT) or on microtitre plates, for example of polystyrene, or on particles, for example magnetic particles, while a further antibody specific for DHRS4 carries a residue which represents a directly detectable label or permits selective linkage to a label and serves for the detection of the sandwich structures formed. Delayed or subsequent immobilization with the use of suitable solid phases is also possible.

It is possible in principle to use all marking techniques which can be used in assays of the type described, including marking with radio isotopes, enzymes, fluorescent, chemoluminescent or bioluminescent labels and directly optically detectable colour markings, such as, for example, gold atoms and dye particles, as are used in particular for so-called point-of-care (POC) or accelerated tests. It is therefore within the scope of the present invention to design the method according to the invention also as an accelerated test.

The method for determining DHRS4 can also be carried out, for example, using a homogeneous detection method in which sandwich complexes formed from two antibodies and the DHRS4 to be detected remain suspended in the liquid phase. In such a case, it is preferable to mark both antibodies with parts of a detection system which permits signal generation or signal triggering when both antibodies are integrated in a single sandwich. Such techniques can be designed in particular as fluorescence amplification or fluorescence extinction detection methods. A particularly preferred method of this type relates to the use of detection reagents to be used in pairs, as described, for example, in U.S. Pat. No. 4,822,733, EP-B1-180 492 or EP-B1-539 477 and the prior art cited therein. They permit a measurement which selectively detects only reaction products which contain both marking components in a single immune complex, directly in the reaction mixture. As an example, reference may be made to the technology which is offered under the brands TRACE® (Time Resolved Amplified Cryptate Emission) and KRYPTOR® and which implement the teachings of the abovementioned Applications.

However, in the case of heterogeneous sandwich immunoassays too, two antibodies specific for DHRS4 can have parts of a detection system of the type just described in connection with homogeneous assays.

As shown below, the occurrence of DHRS4—in the context of a detectable expression—in baboon liver extracts is coupled to a preceding "sepsis"—inducing endotoxin stimulus and a preceding infection. In untreated controls, no DHRS4 detection is possible, in agreement with the literature cited at the outset. DHRS4 is therefore a potential sepsis marker.

Below, the invention is explained in more detail with reference to seven figures.

In the figures:

FIG. 1 shows enlarged sections of 2D gels which permit a comparison of the spot samples of soluble liver proteins of a healthy baboon (A) with the liver proteins of a baboon 5 h after a sepsis induced by injection of LPS (B). The circle indicates the position of the sepsis-specific product DHRS4 according to the invention.

Figure 2A:
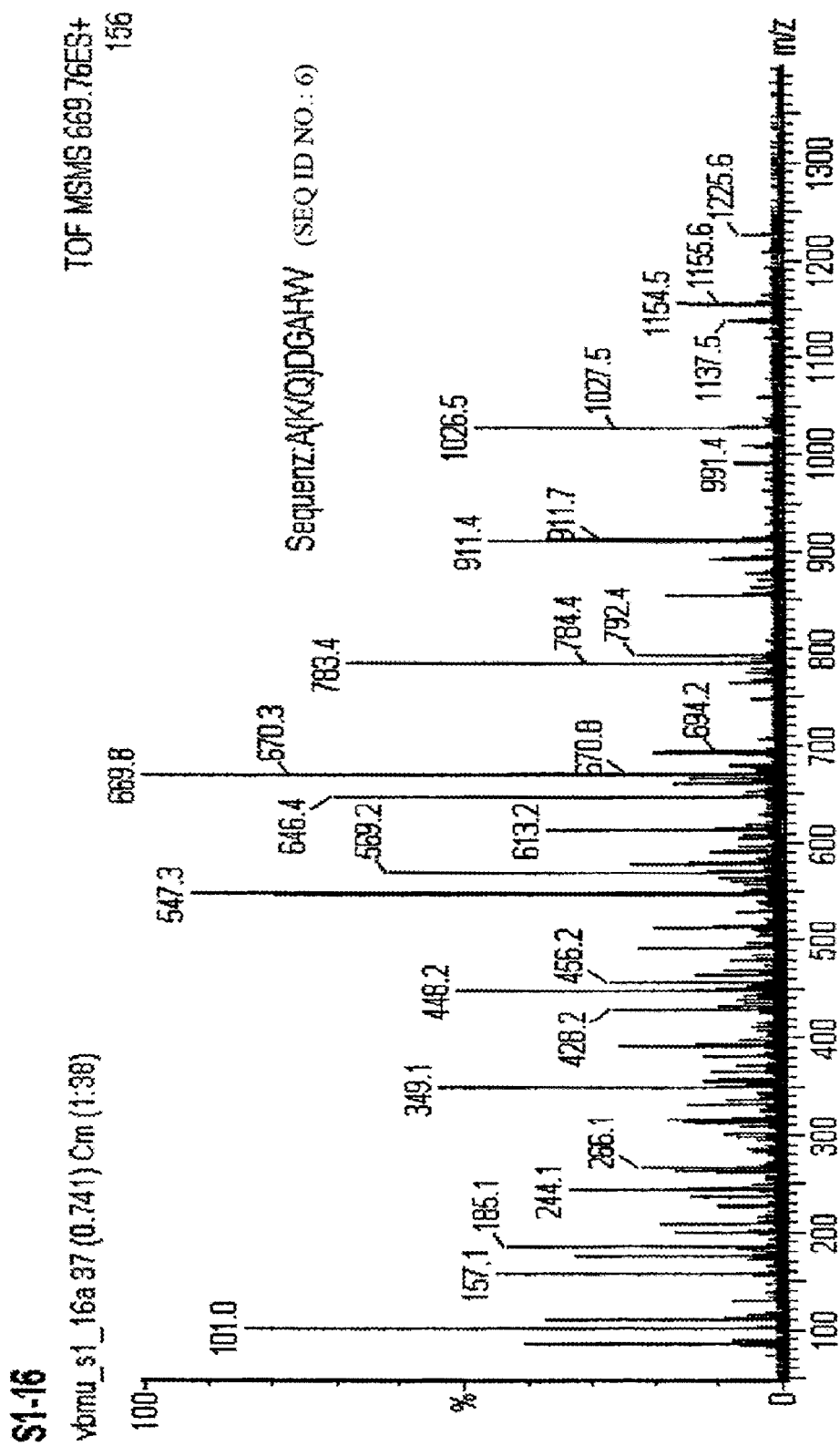

FIG. 2A shows results of an ESI-MS/MS tandem mass spectrometry of a selected peptide fragment of the trypsin digestion of the sepsis-specific protein spot. Tandem mass spectrum of the precursor ion=669.76. The interpretation of the spectrum results in the amino acid sequence A (K/Q) DGAHVV (SEQ ID NO.: 6).

Figure 2B:
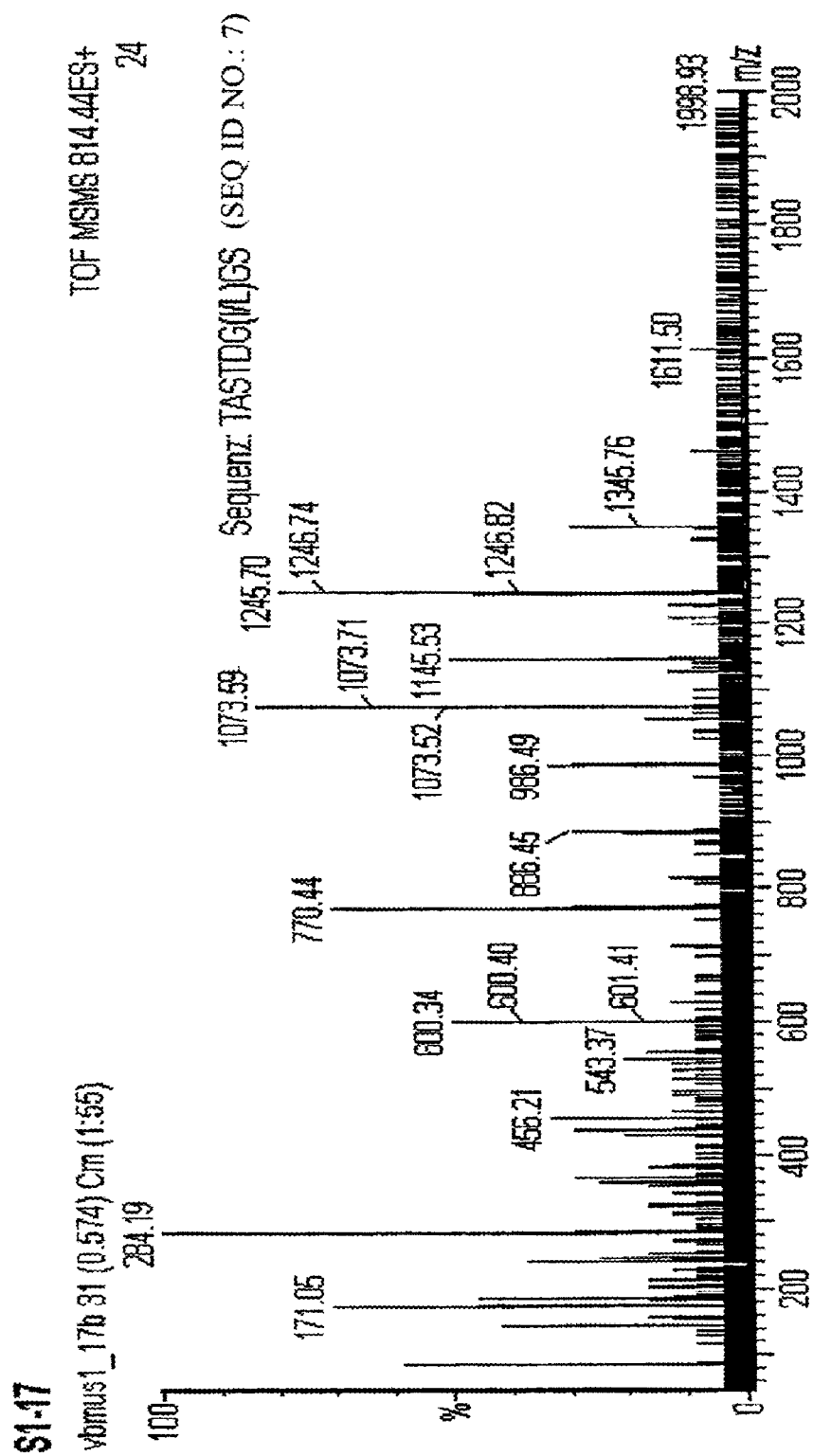

FIG. 2B shows results of an ESI-MS/MS tandem mass spectrometry of a selected peptide fragment of the trypsin digestion of the sepsis-specific protein spot. Tandem mass spectrum of the precursor ion=814.44. The interpretation of the spectrum results in the amino acid sequence TASTDG(I/L)GS (SEQ ID NO.: 7).

FIG. 3 shows the amino acid sequence of DHRS4 (cf. also SEQ ID No: 1). Structural elements of interest are emphasized: probable β-folded sheet structures and α-helices were identified with the sequences stated in Kalberg Y et al., (2002) (15) and in Jörnvall H et al., (1995) (1) and are outlined. Conserved amino acids were identified by the same comparison; these have a shaded background. For other members of the SDR family, it was stated that contact points in the case of a multimerisation are the regions α4(E) and α5(F). Jörnvall H et al., (1995) (1). According to a sequence comparison with DHS2 (SWISSPROT) entry Q13268) a binding site for NAD/NADP is the region of positions 36-59.

Sequence regions which were used as peptides for immunization are shown in bold and italics (positions 19-30, 209-228, 230-247, 256-278).

Figure 4:
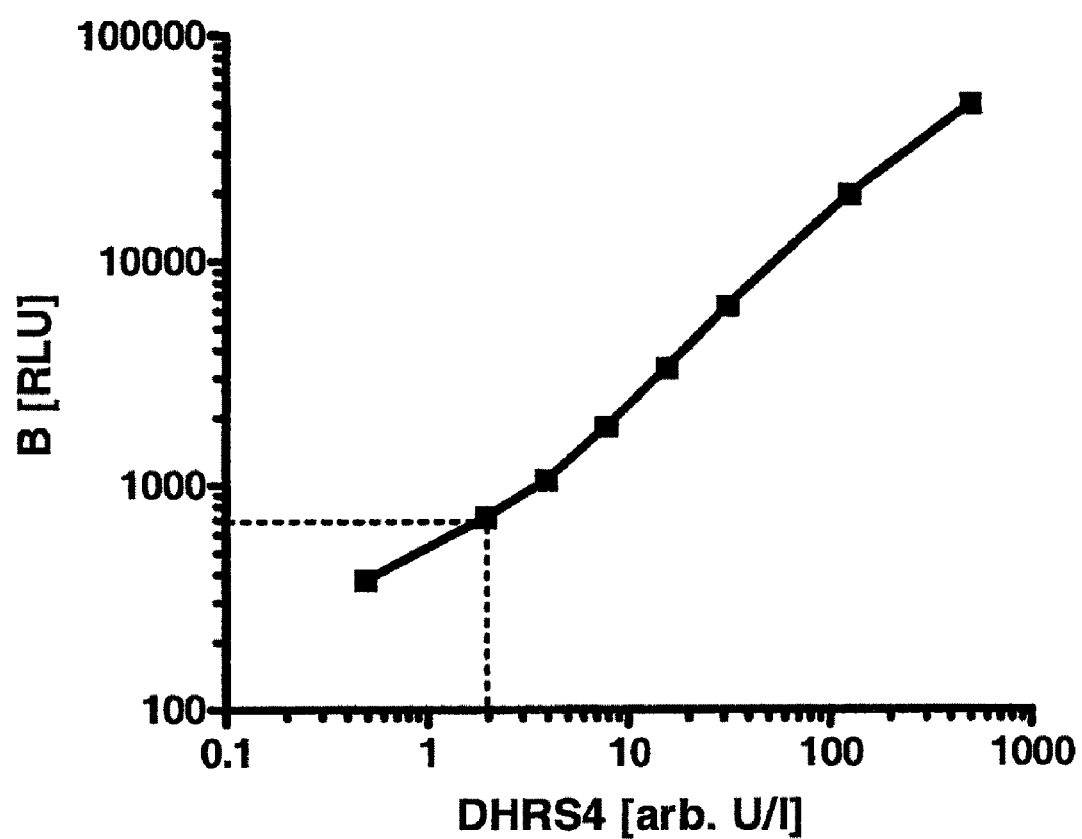

FIG. 4 shows a typical standard curve of the DHRS4 sandwich immunoassay used in section 5.1 for determinations in the present Application (chemiluminescence assay in coated tube format; antibodies against the regions of positions 209-228—peptide PLE20; solid phase) and 256-278 (peptide PSL23; tracer). Dilutions of recombinant DHRS4-containing *E. coli* extract in horse normal serum served as standards to which arbitrary units were ascribed. The functional assay sensitivity of 2 V/L is indicated.

Figure 5:
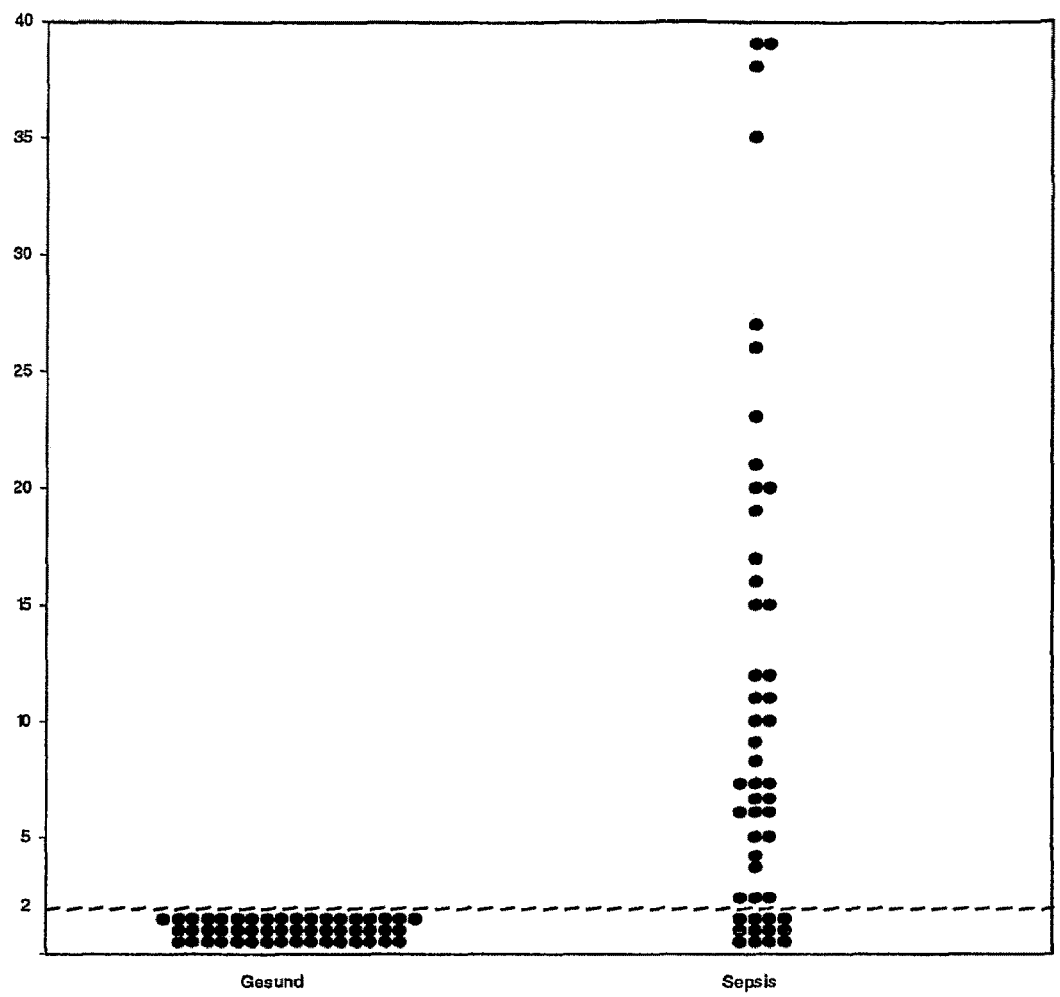

FIG. 5 shows DHRS4 immunoreactivities measured with an assay according to FIG. 4, measured in each case in 50 plasma samples of healthy test persons and sepsis patients. The functional assay sensitivity of 2 U/l is indicated.

Figure 6A:
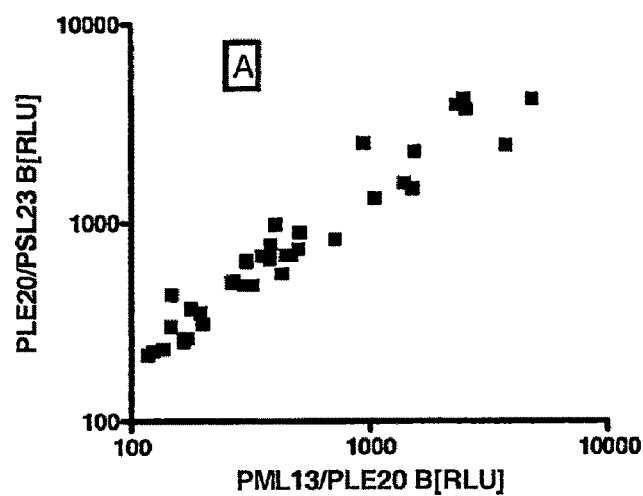
Figure 6B:
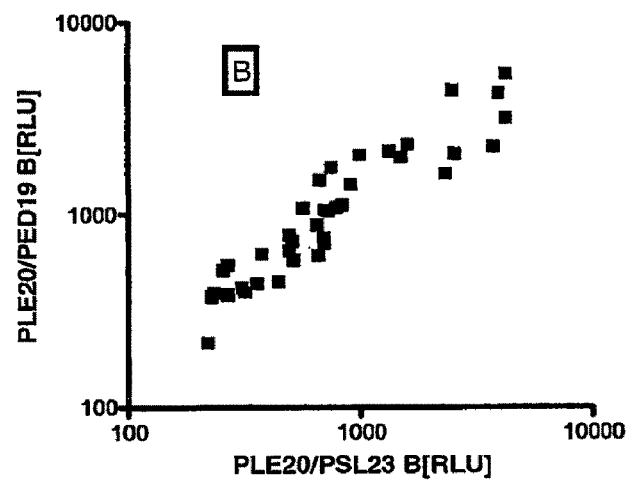
Figure 6C:
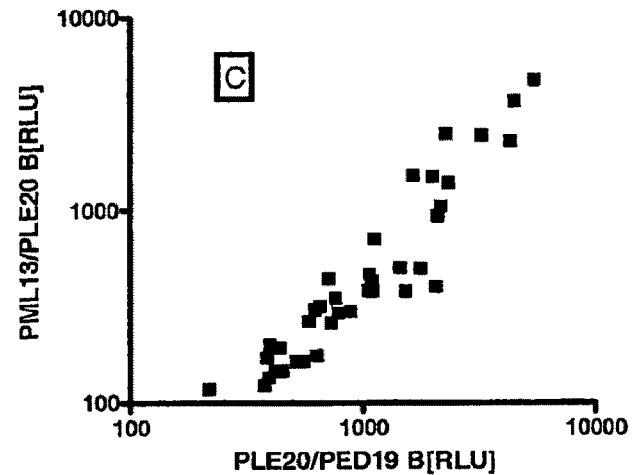

FIG. 6 shows a comparison of methods for different sandwich assays for DHRS4: plasma samples were measured in different assays. The peptide epitopes of the antibodies used in the assays are indicated on the axes. The correlation coefficients are: r=0.97 (A), r=0.95 (B), r=0.94 (C).

FIG. 7A shows a sequence comparison of DHRS4 (DHS4_HUMAN) with the sequence DHS2_HUMAN (program ClustalW). Identical amino acids are characterized by asterisks; structurally related amino acids are characterized by dots. Those sequence regions of DHRS4 which were synthesised as peptides and used for the production of antibodies are marked.

FIG. 7B shows a sequence comparison of DHRS4 (DHS4_HUMAN) with two splicing variants identified in the database SWISSPROT (program ClustalW). Identical amino acids are characterized by asterisks. Those sequence regions of DHRS4 which were synthesised as peptides and used for the production of antibodies are marked.

EXPERIMENTAL RESULTS

1. Infection Simulation By Endotoxin Administration in the Animal Model (Baboons)

With regard to the tests carried out with baboons for stimulating procalcitonin secretion by endotoxin injections (5, 6), male baboons (*Papio ursinus*), about 2 years old, weighing 27 to 29 kg, were each intravenously administered 100 µg of LPS (lipopolysaccharide from *Salmonella typhimurium*, source: Sigma) per kg body weight. 5 to 5.5 h after the injection, the animals were sacrificed by intravenous administration of 10 ml of doletal. Immediately after their death, the liver was prepared and was stabilized by freezing in liquid nitrogen.

In the further processing, samples of the frozen livers (1 g) were mixed with 1.5 ml of buffer A (50 mM Tris/HCl, pH 7.1, 100 mM KCl, 20% glycerol, 1 mM Pefabloc, protease inhibitor cocktail "Complete" (Roche): per 1.5 ml of buffer A: 0.2 µl of a solution of 1 tablet in 2 ml) while cooling with nitrogen and were pulverized in a porcelain mortar to give a meal (7). The homogenate was treated with ultrasound for 6×10 sec in a water bath and centrifuged for 40 min at 100,000 g and 4° C., and the supernatant obtained was isolated. The remaining cell pellet was pulverized again as described above under nitrogen, treated with ultrasound and centrifuged. The second supernatant resulting therefrom was combined with the first supernatant and stored at −80° C. until required for further processing.

2. Comparative Proteome Analysis Using Liver Extracts of Baboons

Liver protein extracts of healthy baboons on the one hand (control) and, on the other hand, baboons which had been injected with LPS were used for the proteome analysis. In the analytical 2D gel electrophoresis, liver extract containing 150 µg of protein, was adjusted to 9 M urea, 70 mM DTT, 2% ampholyte pH 2-5 and then separated by means of analytical 2D gel electrophoresis (8). The visualization of the proteins in the 2D electrophoresis gel was effected by means of silver staining (9).

For evaluation, the protein spot patterns of the samples of untreated animals were compared with the protein spot patterns which resulted from liver tissue samples of treated animals. FIG. 1 shows a comparison of the 2D electrophoresis gels for a control sample (A) and a sample of an animal treated with LPS (B). The additional protein spot in (B) with an apparent molecular weight of about 29,000 Dalton and an apparent isoelectric point of about 8.0 to 8.2 was analyzed by mass spectrometry after the differentially occurring protein identified in the protein spot pattern of the analytical 2D gel electrophoresis had subsequently also been prepared by means of preparative 2D gel electrophoresis with the use of 350 µg of protein.

In the preparative 2D gel electrophoresis, the staining was effected by means of Coomassie Brilliant Blue G250 (10).

The protein spot preselected for the further analysis was cut out of the gel and subjected to trypsin digestion using a published method (11) and the trypsin fragments generated were then analyzed by means of electrospray mass spectrometry (ESI-MS) (12-14). A Q-TOF mass spectrometer with a nanoflow Z-spray ion source from Micromass, UK, was used. The operating instructions of the device manufacturer were followed.

3. Identification of Short-chain SRL Alcohol Dehydrogenase (DHRS4)

In each case individual peptides ("tags") from the parent spectrum of the trypsin-digested protein of the selected spot were identified by ESI-MS/MS. The mass spectra obtained for these fragments could be evaluated computationally in a manner known per se. The database search with the ESI-MS/MS sequence tags was carried out with the aid of MS-Edman (see url falcon.ludwig.ucl.ac.uk/ucsfhtml3.2/msedman.htm), which is localized on the Server Protein Prospector of the University of California, San Francisco Mass Spectrometry Facility.

FIG. 2A shows by way of example the MS/MS results for the peptide with the mass 669.76 and the sequence A(K/Q) DGAHVV (SEQ ID NO.: 6) read out from the spectrum (K and Q cannot be distinguished by mass spectrometry). FIG. 2B shows a further peptide with the mass of 814.44 and the resulting spectrum and amino acid sequence of TASTDG(I/L)GS (SEQ ID NO.: 7) (I and L cannot be distinguished by mass spectrometry).

Both amino acid sequences were compared with all sequences of the mammalian proteins of NCBInr.18.09.00 or NCBInr.6.17.2000 database. The best agreement for both peptides (A(K/Q)DGAHVV(SEQ ID NO.: 6) and TASTDG (I/L)GS(SEQ ID NO.: 7)) was found with parts of the human protein DHRS4 (peroxisomal short chain alcohol dehydrogenase): AQDGAHVV (SEQ ID NO.: 6) and TASTDGIGF (SEQ ID NO.: 7). This identification is to be regarded as unambiguous. For human DHRS4 (SEQ ID No: 1), a molecular weight of 29.5 kTa and an isoelectric point of 8.8 can be calculated. These values are very close to the experimentally observed values (see above) and support the identification result.

On the basis of the great similarity of the pathophysiological reactions of baboons and humans, which has in particular also been found again and again in the Applicant's numerous investigations discussed above and which are based on the results of an artificially induced sepsis in baboons, it may be assumed that the conditions occurring in infected or septic human patients are substantial identical to those in the baboon animal model described. This basic assumption was confirmed by immunodiagnostic determination of DHRS4 in human plasmas of healthy persons and sepsis patients.

For this purpose, sandwich immunoassays for DHRS4 were developed and the occurrence of DHRS4 in the blood circulation of various patient groups was investigated therewith.

4. Preparation of Assay Components for DHRS4 Immunoassays

4.1 Peptide Syntheses

For the production of antibodies against DHRS4, partial peptides were synthesised from the amino acid sequence of DHRS4, and sheep were immunized therewith. (FIG. 3). In choosing the peptides, information on the secondary, tertiary and quaternary structure of the protein was taken in to account, with the aim of producing antibodies which are suitable for binding natural DHRS4.

Derived from the known amino acid sequence of DHRS4, four regions were selected (positions 19-30, 209-228, 230-247, 256-278). The regions were (positions 19-30 and 230-247 in each case supplemented by a N-terminal cysteine residue) chemically synthesised as soluble peptides by standard methods, purified, quality-controlled by means of mass spectrometry and reversed-phase HPLC and lyophilised in aliquots (JERINI AG, Berlin, Germany). The amino acid sequences of the peptides were:

```
PML      CMASSGMTRRDPL           (SEQ ID No: 2)
PLE20    CLAPGLIKTSFSRMLWMDKE    (SEQ ID No: 3)
PED19    CEESMKETLRIRRLGEPED     (SEQ ID No: 4)
PSL23    CSEDASYITGETVVVGGGTPSRL (SEQ ID No: 5)
```

4.2 Conjugation and Immunization

The peptides PML13, PLE20, PED19 and PSL23 were conjugated with the carrier protein KLH (keyhole limpet haemocyanine) by means of MBS (m-maleimidobenzoyl-N-hydroxysuccinimide ester) (cf. operating instructions "NHS-esters-maleimide crosslinkers" from PIERCE, Rockford, Ill., USA). Sheep were immunized with these conjugates according to the following scheme: each sheep initially received 100 μg of conjugate (stated mass based on the peptide fraction of the conjugate) and then in each case 50 μg of conjugate every four weeks (stated mass based on the peptide fraction of the conjugate). Beginning with the fourth month after the beginning of the immunization, 700 ml of blood were taken per sheep every four weeks and antiserum was obtained therefrom by centrifuging. Conjugations, immunizations and isolation of antisera were carried out by MicroPharm, Carmarthenshire, UK.

4.3 Purification of the Antibodies

The peptide-specific antibodies were prepared in a 1-step method from the antisera which had been obtained beginning with the fourth month after the immunization.

For this purpose, the peptides PML13, PLE20, PED19 and PSL23 were first coupled to SulfoLink gel (cf. operating instructions "SulfoLink Kit" from PIERCE, Rockford, Ill., USA). In each case 5 mg of peptide were offered per 5 ml of gel for coupling.

The affinity purification of peptide-specific antibodies from sheep antisera against the peptides was carried out as follows:

The peptide columns were first washed three times alternately with 10 ml each of elution buffer (50 mM citric acid, pH 2.2) and binding buffer (100 mM sodium phosphate, 0.1% Tween, pH 6.8). 100 ml of the anti-sera were filtered over 0.2 μm and the existing column material was added to them. For this purpose, the gel was washed from the column quantitatively with 10 ml of binding buffer. The incubation was effected overnight at room temperature with swirling. The batches were transferred quantitatively to empty columns (NAP25, Pharmacia, emptied). The runnings were discarded. The columns were then washed protein-free with 250 ml of binding buffer (protein content of the wash eluate<0.02 A 280 nm). Elution buffer was added to the washed columns, and 1 ml fractions were collected. The protein content of each fraction was determined by means of the BCA method (cf. operating instructions for PIERCE, Rockford, Ill., USA). Fractions having protein concentrations>0.8 mg/ml were pooled. After protein determination of the pools by means of the BCA method yields of 57 mg were obtained for the anti-PML13 antibody, 56 mg for the anti-PLE20 antibody, 12 mg for the anti-PED19 antibody and 99 mg for the anti-PSL23 antibody.

4.4 Antibody marking

By means of NAP-5 gel filtration columns (Pharmacia) 500 μl of each of the purified anti-PLE20, anti-PED19 and anti-PSL23 antibodies (see above) were rebuffered in 1 ml of 100 mM potassium phosphate buffer (pH 8.0) in each case. The protein concentrations of the antibody solutions were adjusted to 1.5 mg/ml with 100 mM potassium phosphate buffer (pH 8.0).

For chemiluminescence marking, all antibodies were further treated as follows: 10 μl of MA70 acridinium NHS ester (1 mg/ml; from HOECHST Behring) were added to 67 μl of the antibody solution and incubation was effected for 15 minutes at room temperature. Thereafter, 423 μl of 1 M glycine were added and incubation was effected for a further 10 minutes. Thereafter, the marking batch was rebuffered by means of an NAP-5 gel filtration column (Pharmacia) in 1 ml of mobile phase A (50 mM potassium phosphate, 100 mM NaCl, pH 7.4) according to operating instructions and were freed from low molecular weight constituents thereby. For separating off final residues of labels not bound to antibodies, a gel filtration HPLC was carried out (column: Walters Protein Pak SW300). The sample was applied and was chromatographed at a flow rate of 1 ml/min with mobile phase A. The wavelengths 280 nm and 368 nm were measured using a flow-through photometer. The absorption ratio 368 nm/280 nm as a measure of the degree of marking of the antibody was 0.10+/−0.01 at the peak. The monomeric antibody-containing fractions (retention time 8-10 min) were gathered and were collected in 3 ml 100 mM sodium phosphate, 150 mM NaCl, 5% bovine serum albumin, 0.1% sodium azide, pH 7.4.

4.5 Antibody immobilization

Irradiated 5 ml polystyrene tubes (from Greiner) were coated with purified anti-PML13 antibody or anti-PLE20 antibody as follows: the antibody was diluted to a concentration of 6.6 μg/ml in 50 mM Tris, 100 mM NaCl, pH 7.8. 300 μl of the solution were pipetted into each tube. The tubes were incubated for 20 hours at 22° C. The solution was sucked up. Each tube was then filled with 4.2 ml of 10 mM sodium phosphate, 2% Karion FP, 0.3% bovine serum albumin, pH 6.5. After 20 hours, the solution was sucked up. Finally, the tubes were dried in a vacuum dryer.

5. Procedure and Evaluation of DHRS4 Immunoassays

5.1 Determination of DHRS4 in Human Plasmas

First, a sandwich immunoassay for DHRS4 (antibody against the regions of positions 209-228 or peptide PLE20 and 256-278 or peptide PSL23) having a functional assay sensitivity of about 2 U/l was developed (typical standard curve: cf. FIG. 4).

Plasma samples of healthy persons and sepsis patients were measured using this assay (FIG. 5). All samples of healthy persons gave measured values below the functional assay sensitivity; 38 of the 50 samples of sepsis patients gave measured values above the functional assay sensitivity. A diagnostic sensitivity of 76% at 100% specificity results.

5.2 Immunodiagnostic Determination of DHRS4 in Human Sera—Comparison of Methods

In a comparison of methods, it was found that sandwich assays which use antibodies against other epitopes of DHRS4 lead to results comparable with the assay used under 5.1 (FIG. 6).

For this purpose, a total of three sandwich immunoassays for DHRS4 were established, operating with the following antibodies:
  a) Solid phase: Anti-PLE20, tracer: anti-PSL23 (cf. 5.1).
  b) Solid phase: Anti-PLE20, tracer: anti-PED19
  c) Solid phase: Anti-PML13, tracer: anti-PLE20

The standard material used in each case was recombinant human DHRS4 in the form of an extract from transformed E-coli bacteria (InVivo GmbH, Hennigsdorf, Germany). Cloning and expression of the DHRS4 gene were effected by standard methods of molecular biology. The extract was diluted serially in horse normal serum (from Sigma). Concentrations in arbitrary units were ascribed to the standards thus produced.

Measured samples were EDTA plasmas of apparently healthy persons and of patients suffering from sepsis.

The three sandwich immunoassays were prepared in the same manner as follows: 100 µl of standards or samples and 100 µl of assay buffer (100 mM sodium phosphate, 150 mM NaCl, 5% bovine serum albumin, 0.1% unspecific sheep IgG, 0.1% sodium azide, pH 7.4), containing 1 million RLU (relative light units) of the respective MA70-marked antibody, were pipetted into the respective test tubes coated with antibodies. Incubation was effected for 20 hours at 22° C. with shaking. Thereafter, washing was effected four times with 1 ml each of wash solution 0.1% Tween 20) per tube, the tubes were allowed to drip and the chemiluminescence bound to the tube was measured in a luminometer (from BERTHOLD, LB952T; base reagents from BRAHMS AG).

Using the software MultiCalc (spline fit) the DHRS4 concentrations of the samples were read from the standard curve.

5.3 Estimation of Possible Interfering Influences for the Immunodiagnostic DHRS4 Determination In order to estimate whether antibodies which were produced against the selected peptides could also cross-react with human proteins/peptides other than DHRS4 (SCAD-SLR), DHRS4 was compared with all human sequences present in the SWISSPROT database, by means of "Quickblast". Those sequences found which have similarity with DHRS4 and which contained regions which correspond to epitopes for those antibodies which were used in the three sandwich assay variants carried out were analysed in more detail. Two splicing variants of DHRS4, and the product of the DHRS2 gene, were found (FIG. 7a, 7b). Cross reactivity with the two splicing variants would be expected if the anti-PLE20 antibody too would recognise only the sequence LWMDKE (SEQ ID NO.: 12) (which was not investigated experimentally). However, owing to the low sequence homology, a cross-reactivity with the product of the DHRS2 gene appears improbable but cannot be completely ruled out.

Since it is not known whether and in which concentrations DHRS4 are also present in blood cells, but this is relevant for sampling (haemolysis, incomplete separation of thrombocytes), EDTA blood of normal test persons was completely haemolysed by ultrasound and then measured with respect to DHRS4. Concentrations of 1-3 U/l were detected (data not shown). This shows that DHRS4 is present in blood cells but in such low concentrations that partial haemolysis or partial incomplete separation of thrombocytes has no relevant influence on measured results.

What remains unclear is the mechanism by means of which DHRS4 enters the blood circulation during sepsis.

LIST OF REFERENCES

1. Jornvall, H., Persson, B., Krook, M., Atrian, S., Gonzalez-Duarte, R., Jeffery, J., and Ghosh, D. 1995. Short-chain dehydrogenases/reductases (SDR). *Biochemistry* 34:6003-6013.
2. Clark, H. F., Gurney, A. L., Abaya, E., Baker, K., Baldwin, D., Brush, J., Chen, J., Chow, B., Chui, C., Crowley, C., et al. 2003. The secreted protein discovery initiative (SPDI), a large-scale effort to identify novel human secreted and transmembrane proteins: a bioinformatics assessment. *Genome Res* 13:2265-2270.
3. Fransen, M., Van Veldhoven, P. P., and Subramani, S. 1999. Identification of peroxisomal proteins by using M13 phage protein VI phage display: molecular evidence that mammalian peroxisomes contain a 2,4-dienoyl-CoA reductase. *Biochem J* 340 (Pt 2):561-568.
4. Gould, S. J., Keller, G. A., Hosken, N., Wilkinson, J., and Subramani, S. 1989. A conserved tripeptide sorts proteins to peroxisomes. *J Cell Biol* 108:1657-1664.
5. Redl, H., Schlag, G., Togel, E., Assicot, M., and Bohuon, C. 2000. Procalcitonin release patterns in a baboon model of trauma and sepsis: relationship to cytokines and neopterin. *Crit Care Med* 28:3659-3663.
6. Redl, H., and Schlag, G. 1998. Non-human primate models of sepsis. *Sepsis* 2:243-253.
7. Klose, J. 1999. Fractionated extraction of total tissue proteins from mouse and human for 2-D electrophoresis. *Methods Mol Biol* 112:67-85.
8. Klose, J., and Kobalz, U. 1995. Two-dimensional electrophoresis of proteins: an updated protocol and implications for a functional analysis of the genome. *Electrophoresis* 16:1034-1059.
9. Heukeshoven, J., and Dernick, R. 1988. Improved silver staining procedure for fast staining in PhastSystem Development Unit. I. Staining of sodium dodecyl sulfate gels. *Electrophoresis* 9:28-32.
10. Neuhoff, V., Arold, N., Taube, D., and Ehrhardt, W. 1988. Improved staining of proteins in polyacrylamide gels including isoelectric focusing gels with clear background at nanogram sensitivity using Coomassie Brilliant Blue G-250 and R-250. *Electrophoresis* 9:255-262.
11. Otto, A., Thiede, B., Muller, E. C., Scheler, C., Wittmann-Liebold, B., and Jungblut, P. 1996. Identification of human myocardial proteins separated by two-dimensional electrophoresis using an effective sample preparation for mass spectrometry. *Electrophoresis* 17:1643-1650.
12. Neubauer, G., King, A., Rappsilber, J., Calvio, C., Watson, M., Ajuh, P., Sleeman, J., Lamond, A., and Mann, M. 1998. Mass spectrometry and EST-database searching allows characterization of the multi-protein spliceosome complex. *Nat Genet* 20:46-50.
13. Lingner, J., Hughes, T. R., Shevchenko, A., Mann, M., Lundblad, V., and Cech, T. R. 1997. Reverse transcriptase motifs in the catalytic subunit of telomerase. *Science* 276: 561-567.
14. Mann, M., and Pandey, A. 2001. Use of mass spectrometry-derived data to annotate nucleotide and protein sequence databases. *Trends Biochem Sci* 26:54-61.
15. Kallberg, Y., Oppermann U., Jörnvall H. and Persson, B., *Eur. J. Biochem.* 269, 4409-4417 (2002)

The invention claimed is:

1. An ex vivo method for detection of sepsis, the method comprising:
   determining the amount of short-chain SRL alcohol dehydrogenase (DHRS4) having the amino acid sequence of SEQ ID NO: 1 in a serum or plasma sample from a patient in whom sepsis is suspected;
   wherein an increased amount of short-chain SRL alcohol dehydrogenase (DHRS4) compared to the amount in healthy individuals indicates the presence of sepsis.

2. The method according to claim 1, wherein said method is an immunodiagnostic assay method.

3. The method according to claim 2, wherein said method is a heterogeneous or homogeneous immunodiagnostic assay method in the form of a sandwich assay.

4. The method of claim 1, wherein said method is carried out as part of a multi-parameter determination in which at least one further sepsis parameter is determined.

* * * * *

SEQUENCE LISTING

<160> NUMBER OF SEQ ID NOS: 12

<210> SEQ ID NO 1
<211> LENGTH: 278
<212> TYPE: PRT
<213> ORGANISM: Homo sapiens

<400> SEQUENCE: 1

```
Met His Lys Ala Gly Leu Leu Gly Leu Cys Ala Arg Ala Trp Asn Ser
1               5                   10                  15

Val Arg Met Ala Ser Ser Gly Met Thr Arg Arg Asp Pro Leu Ala Asn
            20                  25                  30

Lys Val Ala Leu Val Thr Ala Ser Thr Asp Gly Ile Gly Phe Ala Ile
        35                  40                  45

Ala Arg Arg Leu Ala Gln Asp Gly Ala His Val Val Ser Ser Arg
    50                  55                  60

Lys Gln Gln Asn Val Asp Gln Ala Val Ala Thr Leu Gln Gly Glu Gly
65                  70                  75                  80

Leu Ser Val Thr Gly Thr Val Cys His Val Gly Lys Ala Glu Asp Arg
                85                  90                  95

Glu Arg Leu Val Ala Thr Ala Val Lys Leu His Gly Gly Ile Asp Ile
            100                 105                 110

Leu Val Ser Asn Ala Ala Val Asn Pro Phe Phe Gly Ser Ile Met Asp
        115                 120                 125

Val Thr Glu Glu Val Trp Asp Lys Thr Leu Asp Ile Asn Val Lys Ala
130                 135                 140

Pro Ala Leu Met Thr Lys Ala Val Val Pro Glu Met Glu Lys Arg Gly
145                 150                 155                 160

Gly Gly Ser Val Val Ile Val Ser Ser Ile Ala Ala Phe Ser Pro Ser
                165                 170                 175

Pro Gly Phe Ser Pro Tyr Asn Val Ser Lys Thr Ala Leu Leu Gly Leu
            180                 185                 190

Thr Lys Thr Leu Ala Ile Glu Leu Ala Pro Arg Asn Ile Arg Val Asn
        195                 200                 205

Cys Leu Ala Pro Gly Leu Ile Lys Thr Ser Phe Ser Arg Met Leu Trp
    210                 215                 220

Met Asp Lys Glu Lys Glu Ser Met Lys Glu Thr Leu Arg Ile Arg
225                 230                 235                 240

Arg Leu Gly Glu Pro Glu Asp Cys Ala Gly Ile Val Ser Phe Leu Cys
                245                 250                 255

Ser Glu Asp Ala Ser Tyr Ile Thr Gly Glu Thr Val Val Val Gly Gly
            260                 265                 270

Gly Thr Pro Ser Arg Leu
        275
```

<210> SEQ ID NO 2
<211> LENGTH: 13
<212> TYPE: PRT
<213> ORGANISM: Artifical Sequence
<220> FEATURE:
<221> NAME/KEY: misc_feature
<222> LOCATION: (1)..(13)
<223> OTHER INFORMATION: synthetic peptide

<400> SEQUENCE: 2

```
Cys Met Ala Ser Ser Gly Met Thr Arg Arg Asp Pro Leu
1               5                   10
```

```
<210> SEQ ID NO 3
<211> LENGTH: 20
<212> TYPE: PRT
<213> ORGANISM: Artifical Sequence
<220> FEATURE:
<221> NAME/KEY: misc_feature
<222> LOCATION: (1)..(20)
<223> OTHER INFORMATION: synthetic peptide

<400> SEQUENCE: 3

Cys Leu Ala Pro Gly Leu Ile Lys Thr Ser Phe Ser Arg Met Leu Trp
1               5                   10                  15

Met Asp Lys Glu
            20

<210> SEQ ID NO 4
<211> LENGTH: 19
<212> TYPE: PRT
<213> ORGANISM: Artifical Sequence
<220> FEATURE:
<221> NAME/KEY: misc_feature
<222> LOCATION: (1)..(19)
<223> OTHER INFORMATION: synthetic peptide

<400> SEQUENCE: 4

Cys Glu Glu Ser Met Lys Glu Thr Leu Arg Ile Arg Arg Leu Gly Glu
1               5                   10                  15

Pro Glu Asp

<210> SEQ ID NO 5
<211> LENGTH: 23
<212> TYPE: PRT
<213> ORGANISM: Artifical Sequence
<220> FEATURE:
<221> NAME/KEY: misc_feature
<222> LOCATION: (1)..(23)
<223> OTHER INFORMATION: synthetic peptide

<400> SEQUENCE: 5

Cys Ser Glu Asp Ala Ser Tyr Ile Thr Gly Glu Thr Val Val Val Gly
1               5                   10                  15

Gly Gly Thr Pro Ser Arg Leu
            20

<210> SEQ ID NO 6
<211> LENGTH: 7
<212> TYPE: PRT
<213> ORGANISM: Artifical Sequence
<220> FEATURE:
<221> NAME/KEY: misc_feature
<222> LOCATION: (1)..(7)
<223> OTHER INFORMATION: synthetic peptide
<220> FEATURE:
<221> NAME/KEY: misc_feature
<222> LOCATION: (2)..(2)
<223> OTHER INFORMATION: Xaa can be K or Q

<400> SEQUENCE: 6

Ala Xaa Asp Gly Ala His Trp
1               5

<210> SEQ ID NO 7
<211> LENGTH: 9
<212> TYPE: PRT
<213> ORGANISM: Artifical Sequence
<220> FEATURE:
<221> NAME/KEY: misc_feature
```

```
<222> LOCATION: (1)..(9)
<223> OTHER INFORMATION: synthetic peptide
<220> FEATURE:
<221> NAME/KEY: MISC_FEATURE
<222> LOCATION: (7)..(7)
<223> OTHER INFORMATION: Xaa can be I or L

<400> SEQUENCE: 7

Thr Ala Ser Thr Asp Gly Xaa Gly Ser
1               5

<210> SEQ ID NO 8
<211> LENGTH: 258
<212> TYPE: PRT
<213> ORGANISM: Homo sapiens

<400> SEQUENCE: 8

Ser Ser Thr Gly Ile Asp Arg Lys Gly Val Leu Ala Asn Arg Val Ala
1               5                   10                  15

Val Val Thr Gly Ser Thr Ser Gly Ile Gly Phe Ala Ile Ala Arg Arg
            20                  25                  30

Leu Ala Arg Asp Gly Ala His Val Val Ile Ser Ser Arg Lys Gln Gln
        35                  40                  45

Asn Val Asp Arg Ala Met Ala Lys Lys Leu Gln Gly Glu Gly Leu Ser
    50                  55                  60

Val Ala Gly Ile Val Cys His Val Gly Lys Ala Glu Asp Arg Glu Gln
65                  70                  75                  80

Leu Val Ala Lys Ala Leu Glu His Cys Gly Gly Val Asp Phe Leu Val
                85                  90                  95

Cys Ser Ala Gly Val Asn Pro Leu Val Gly Ser Thr Leu Gly Thr Ser
            100                 105                 110

Glu Gln Ile Trp Asp Lys Ile Leu Ser Val Asn Val Lys Ser Pro Ala
        115                 120                 125

Leu Leu Leu Ser Gln Leu Leu Pro Tyr Met Glu Asn Arg Arg Gly Ala
    130                 135                 140

Val Ile Leu Val Ser Ser Ile Ala Ala Tyr Asn Pro Val Val Ala Leu
145                 150                 155                 160

Gly Val Tyr Asn Val Ser Lys Thr Ala Leu Leu Gly Leu Thr Arg Thr
                165                 170                 175

Leu Ala Leu Glu Leu Ala Pro Asp Lys Ile Arg Val Asn Cys Val Val
            180                 185                 190

Pro Gly Ile Ile Lys Thr Asp Phe Ser Lys Val Phe His Gly Asn Glu
        195                 200                 205

Ser Leu Trp Lys Asn Phe Lys Glu His His Gln Leu Gln Arg Ile Gly
    210                 215                 220

Glu Ser Glu Asp Cys Ala Gly Ile Val Ser Phe Leu Cys Ser Pro Asp
225                 230                 235                 240

Ala Ser Tyr Val Asn Gly Glu Asn Ile Ala Val Ala Gly Tyr Ser Thr
                245                 250                 255

Arg Leu

<210> SEQ ID NO 9
<211> LENGTH: 174
<212> TYPE: PRT
<213> ORGANISM: Homo sapiens

<400> SEQUENCE: 9

Met Ala Ser Ser Gly Met Thr Arg Arg Asp Pro Leu Ala Asn Lys Val
1               5                   10                  15
```

```
Ala Leu Val Thr Ala Ser Thr Asp Gly Ile Gly Phe Ala Ile Ala Arg
             20                  25                  30

Arg Leu Ala Gln Asp Gly Ala His Val Val Ser Ser Arg Lys Gln
         35                  40                  45

Gln Asn Val Asp Gln Ala Val Ala Thr Leu Gln Gly Glu Gly Leu Ser
     50                  55                  60

Val Thr Gly Thr Val Cys His Val Gly Lys Ala Glu Asp Arg Glu Arg
65                  70                  75                  80

Leu Val Ala Thr Ala Val Lys Leu His Gly Gly Ile Asp Ile Leu Val
                 85                  90                  95

Ser Asn Ala Ala Val Asn Pro Phe Phe Gly Ser Ile Met Asp Val Thr
                100                 105                 110

Glu Glu Val Trp Asp Lys Leu Trp Met Asp Lys Glu Lys Glu Glu Ser
                115                 120                 125

Met Lys Glu Thr Leu Arg Ile Arg Arg Leu Gly Glu Pro Glu Asp Cys
    130                 135                 140

Ala Gly Ile Val Ser Phe Leu Cys Ser Glu Asp Ala Ser Tyr Ile Thr
145                 150                 155                 160

Gly Glu Thr Val Val Gly Gly Gly Thr Pro Ser Leu Arg
                165                 170

<210> SEQ ID NO 10
<211> LENGTH: 140
<212> TYPE: PRT
<213> ORGANISM: Homo sapiens

<400> SEQUENCE: 10

Met Ala Ser Ser Gly Met Thr Arg Arg Asp Pro Leu Ala Asn Lys Val
1               5                   10                  15

Ala Leu Val Thr Ala Ser Thr Asp Gly Ile Gly Phe Ala Ile Ala Arg
             20                  25                  30

Arg Leu Ala Gln Asp Gly Ala His Val Val Ser Ser Arg Lys Gln
         35                  40                  45

Gln Asn Val Asp Gln Ala Val Ala Thr Leu Gln Gly Glu Gly Leu Ser
     50                  55                  60

Val Thr Gly Thr Val Cys His Val Gly Lys Ala Glu Asp Arg Glu Arg
65                  70                  75                  80

Leu Val Ala Thr Leu Trp Met Asp Lys Glu Lys Glu Glu Ser Met Lys
                 85                  90                  95

Glu Thr Leu Arg Ile Arg Arg Leu Gly Glu Pro Glu Asp Cys Ala Gly
                100                 105                 110

Ile Val Ser Phe Leu Cys Ser Glu Asp Ala Ser Tyr Ile Thr Gly Glu
                115                 120                 125

Thr Val Val Gly Gly Gly Thr Pro Ser Arg Leu
    130                 135                 140

<210> SEQ ID NO 11
<211> LENGTH: 260
<212> TYPE: PRT
<213> ORGANISM: Homo sapiens

<400> SEQUENCE: 11

Met Ala Ser Ser Gly Met Thr Arg Arg Asp Pro Leu Ala Asn Lys Val
1               5                   10                  15

Ala Leu Val Thr Ala Ser Thr Asp Gly Ile Gly Phe Ala Ile Ala Arg
             20                  25                  30
```

```
Arg Leu Ala Gln Asp Gly Ala His Val Val Ser Ser Arg Lys Gln
        35                  40                  45

Gln Asn Val Asp Gln Ala Val Ala Thr Leu Gln Gly Glu Gly Leu Ser
    50                  55                  60

Val Thr Gly Thr Val Cys His Val Gly Lys Ala Glu Asp Arg Glu Arg
65                  70                  75                  80

Leu Val Ala Thr Ala Val Lys Leu His Gly Gly Ile Asp Ile Leu Val
                85                  90                  95

Ser Asn Ala Ala Val Asn Pro Phe Phe Gly Ser Ile Met Asp Val Thr
                100                 105                 110

Glu Glu Val Trp Asp Lys Thr Leu Asp Ile Asn Val Lys Ala Pro Ala
            115                 120                 125

Leu Met Thr Lys Ala Val Val Pro Glu Met Glu Lys Arg Gly Gly Gly
        130                 135                 140

Ser Val Val Ile Val Ser Ser Ile Ala Ala Phe Ser Pro Ser Pro Gly
145                 150                 155                 160

Phe Ser Pro Tyr Asn Val Ser Lys Thr Ala Leu Leu Gly Leu Thr Lys
                165                 170                 175

Thr Leu Ala Ile Glu Leu Ala Pro Arg Asn Ile Arg Val Asn Cys Leu
            180                 185                 190

Ala Pro Gly Leu Ile Lys Thr Ser Phe Ser Arg Met Leu Trp Met Asp
        195                 200                 205

Lys Glu Lys Glu Glu Ser Met Lys Glu Thr Leu Arg Ile Arg Arg Leu
    210                 215                 220

Gly Glu Pro Glu Asp Cys Ala Gly Ile Val Ser Phe Leu Cys Ser Glu
225                 230                 235                 240

Asp Ala Ser Tyr Ile Thr Gly Glu Thr Val Val Val Gly Gly Gly Thr
                245                 250                 255

Pro Ser Arg Leu
            260

<210> SEQ ID NO 12
<211> LENGTH: 6
<212> TYPE: PRT
<213> ORGANISM: Artifical Sequence
<220> FEATURE:
<221> NAME/KEY: misc_feature
<222> LOCATION: (1)..(6)
<223> OTHER INFORMATION: synthetic peptide

<400> SEQUENCE: 12

Leu Trp Met Asp Lys Glu
1               5
```